United States Patent
Pless

(10) Patent No.: US 7,174,213 B2
(45) Date of Patent: Feb. 6, 2007

(54) ELECTRICAL STIMULATION STRATEGIES TO REDUCE THE INCIDENCE OF SEIZURES

(76) Inventor: Benjamin D. Pless, 255 Santa Ana Ct., Sunnyvale, CA (US) 94085

( * ) Notice: Subject to any disclaimer, the term of this patent is extended or adjusted under 35 U.S.C. 154(b) by 106 days.

(21) Appl. No.: 09/952,871

(22) Filed: Sep. 11, 2001

(65) Prior Publication Data

US 2002/0072770 A1 Jun. 13, 2002

Related U.S. Application Data

(63) Continuation-in-part of application No. 09/543,450, filed on Apr. 5, 2000.

(51) Int. Cl.
*A61N 1/36* (2006.01)

(52) U.S. Cl. ...................................................... 607/45
(58) Field of Classification Search ................. 607/45, 607/2, 58; 600/544, 545
See application file for complete search history.

(56) References Cited

U.S. PATENT DOCUMENTS

| | | | | | |
|---|---|---|---|---|---|
| 6,427,086 | B1 | * | 7/2002 | Fischell et al. | 607/45 |
| 6,459,936 | B2 | * | 10/2002 | Fischell et al. | 607/45 |
| 6,480,743 | B1 | * | 11/2002 | Kirkpatrick et al. | 607/45 |

* cited by examiner

*Primary Examiner*—Scott M. Getzow

(57) ABSTRACT

An implantable multimodal neurostimulator having improved efficacy in treating epilepsy and other neurological disorders and processes of using that neurostimulator are described herein. The neurostimulator itself generally has two modes of electrical stimulation. The first involves delivering a non-responsive electrical stimulation signal that is applied to the central nervous system to reduce the likelihood of a seizure or other undesirable neurological even from occurring. Various waveform morphologies are described for non-responsive stimulation signals. A second mode involves delivering a responsive electrical stimulation signal when epileptiform waveforms are impending or extant. The responsive electrical stimulation signal is intended to terminate epileptiform activity, e.g., to desynchronize abnormally synchronous brain electrical activity.

24 Claims, 10 Drawing Sheets

ELECTRICAL STIMULATION STRATEGIES TO REDUCE THE INCIDENCE OF SEIZURES

CROSS-REFERENCE TO RELATED APPLICATION

The present invention is a continuation-in-part of U.S. patent application Ser. No. 09/543,450, filed on Apr. 5, 2000.

FIELD OF THE INVENTION

This invention is directed to an implantable neurostimulator having improved efficacy in treating epilepsy and other neurological disorders, and particularly in reducing the incidence of epileptic seizures, and also to processes of using that neurostimulator.

BACKGROUND OF THE INVENTION

Epileptic seizures are characterized by excessive or abnormally synchronous neuronal activity. Neurologists recognize a wide variety of seizures. Partial onset seizures begin in one part of the brain; general onset seizures arise throughout the entire brain simultaneously. When partial onset seizures progress to involve much of the brain, they are said to have "secondarily generalized." Some seizures result in the loss of conscious awareness and are termed "complex" seizures. So-called "simple" seizures may involve other symptoms, but consciousness is unimpaired. Seizure symptoms may include sensory distortions, involuntary movements, or loss of muscle tone. The behavioral features of a seizure will often reflect a function of the cortex where the abnormal electrical activity is found.

Physicians have been able to treat epilepsy by resecting certain brain areas by surgery and by medication. Brain surgery is irreversible, and is ineffective or is associated with neural morbidity in a sizable percentage of cases. Medication is the most prevalent treatment for epilepsy. It is effective in over half of patients, but in the reminder of the patients, the medication is either ineffective in controlling seizures, or the patients suffer from debilitating side effects. A more promising method of treating patients having epileptic seizures is by electrical stimulation of the brain.

Since the early 1970's, electrical brain stimulators have been used to provide more or less constant stimulation, the stimulation largely being unrelated to detected electrical activity.

Electrical stimulation of the nervous system has been used to suppress seizures. A device is described in Cooper et al. for stimulation of the cerebellum. See, "The Effect of Chronic Stimulation of Cerebellar Cortex on Epilepsy and Man," I. S. Cooper et al. in *The Cerebellum, Epilepsy and Behavior*, Cooper, Riklan and Snyder eds., Plenum Press, N.Y., 1974. Others have utilized devices that stimulate the centromedian nucleus of the thalamus. See, "Electrical Stimulation of the Centromedian Thalamic Nucleus in Control of Seizures: Long Term Studies," F. Velasco et al, *Epilepsia*, 36 (1): 63–71, 1995. Chaos Theory has been used to apply stimulation to a seizure focus in vitro to abort the seizure. See S. Schiff et al, "Controlling Chaos in the Brain," *Nature*, 370: 615–620, Aug. 25, 1994.

Non responsive electrical stimulation devices have been used for significant periods. The devices and procedures did not constitute a panacea, however. For instance, a seventeen-year follow-up study shown in Davis et al. ("Cerebellar Stimulation for Seizure Control 17 Year Study," Proceedings of the Meeting of the American Society for Stereotactic and Functional Neurosurgery, Pittsburgh, Pa., Jun. 16–19, 1991 and in *Stereotact. Funct. Neurosurg.* 1992; 58: 200–208) showed that less than one-half of the patients became seizure free, even though 85% showed some benefit.

In contrast, responsive stimulation, specifically electrical stimulation that is applied to the brain, has not yet been used to treat patients in long-term studies. This is true even though there are algorithms suitable for detection of the onset of an epileptic seizure. For instance, Qu et al. provide an algorithm said to recognize patterns of electrical activity similar to those developed while recording an actual epileptic seizure. See, Qu et al., "A Seizure Warning System for Long-Term Epilepsy Monitoring," *Neurology* 1995; 45: 2250–2254. Similarly, Osorio, et al. have suggested an algorithm applied to signals from intracranial electrodes with good results. See Osorio et al., "A Method For Accurate Automated Real-Time Seizure Detection," *Epilepsia* 1995, 36(supp. 4).

None of the cited documents describes procedures in which a non-responsive electrical stimulation signal is applied to the brain in a first mode and, upon detection of impending or of extant epileptiform electrical activity, a second responsive mode of stimulation is applied to the brain either with or without cessation of non-responsive stimulation.

SUMMARY OF THE INVENTION

The neurostimulator disclosed herein itself generally involves two modes of electrical stimulation: the first involves delivering a non-responsive electrical stimulation signal which is applied to the central nervous system to reduce the likelihood of a seizure or other undesirable neurological even from occurring, and a second mode that involves delivering electrical stimulation signal or signals when epileptiform waveforms are impending or extant.

The responsive electrical stimulation signal or signals are intended to terminate epileptiform activity, e.g., to desynchronize abnormally synchronous brain electrical activity.

Alternatively, the second mode may be used to deliver sensory stimulation, e.g., a scalp or sound stimulation, to the patient rather than deliver electrical stimulation to the patient.

Finally, the neurostimulator may be used by a physician to induce epileptiform activity and then verify the effectiveness of the parameters of the neurostimulation signals.

The invention is an implantable neurostimulator having improved efficacy in treating epilepsy and other neurological disorders and processes of using that neurostimulator. The method generally includes three or more steps. Initially, a non-responsive electrical stimulation signal is applied to the brain in a non-responsive mode. Secondly, some brain electrical activity is detected either during the non-responsive stimulation signal or after the non-responsive stimulation signal is paused. Third, when that detected electrical activity shows impending or existing epileptiform brain electrical activity, a second electrical stimulation signal is applied to the brain. Alternatively, a sensory stimulation, e.g., sound or scalp twitch, may be directed to the patient in place of or in addition to the second electrical stimulation signal.

The first or non-responsive electrical stimulation signal may or may not be paused during the second phase as desired. The non-responsive stimulation may be diurnally varied or varied on some other schedule as desired. The brain electrical activity may be detected in a variety of ways including scalp electrodes, cortical electrodes, or the electrical activity may be monitored at a depth within the brain. The responsive electrical stimulation signal may be applied to one or more electrodes placed on or about the brain. If multiple electrodes are chosen, either for measurement of the brain electrical activity or application of the responsive stimulation, the electrodes may be chosen so that they are independently selectable if so desired. The responsive stimulation (and the non-responsive stimulation) may be defined by parameters such as the electrode or electrodes selected, pulse width, inter-pulse interval (or frequency), pulse amplitude, pulse morphology (including the use of continuous waveforms such as trapezoidal, quasi-sinusoidal or sinusoidal morphologies, or pulse morphologies where each phase of the pulse is triangular, trapezoidal, a haversine, or other shape), the number of pulses in the burst (or the number of cycles, if a continuous waveform morphology is used), the number of bursts, and the intervals between bursts. Each of these parameters for either the responsive or the nonresponsive stimulation may be changed or left static during a mode of the process.

The procedure may include a pause of the responsive stimulation for detection of or measurement of brain electrical activity. This may then be followed by either re-commencement of the non-responsive stimulation, or, if the desired cessation of epileptiform activity has not been achieved, by a continuation of the responsive stimulation.

The procedure may also include the step of using the implanted neurostimulator to apply electrical stimulation to the brain under physician control to cause epileptiform activity and a second step of using the implanted neurostimulator to apply a responsive stimulation signal which terminates that epileptiform activity. This permits the neurostimulator to be used to test the effectiveness of the parameters selected for responsive stimulation. The testing may be done before, during, or anytime after implantation of the inventive neurostimulator to assess functionality. In addition, the testing may be used to verify the effectiveness of the nonresponsive stimulation parameters by assessing the relative ease or difficulty in initiating epileptiform activity.

In general, the implantable neurostimulator includes at least a first brain electrical activity sensor near or in contact with the brain, at least a first stimulator electrode for providing a non-responsive stimulation to the brain and optionally for providing the responsive stimulation, a non-responsive signal source for the first stimulation electrode, one or more (optional) second stimulator electrodes for providing the responsive stimulation, and a responsive stimulation source. The non-responsive and responsive sources may be integrated into a single source if so desired.

Desirably there may be one, two or multiple brain electrodes. When one electrode is used, the electrode is placed in a location in the brain that is best suited to terminating the patient's seizure with the responsive mode stimulation (typically near the epileptogenic region or a neural pathway involved in sustaining or propagating epileptiform activity which may be within a neural relay such as a thalamic structure). If there are two electrodes, the first is used for non-responsive stimulation and positioned in or on the cerebellum or in a deep brain structure such as the thalamus, basal ganglia and related structures, hippocampus or amygdala, the second used for responsive stimulation and placed on or near the seizure focus or a neural pathway involved in sustaining or propagating the epileptiform activity. In some variations of the invention, the patient will benefit from a larger number of electrodes being used. In addition to the responsive mode stimulation, scheduled stimulation is delivered to reduce the incidence of spontaneously arising seizures.

A neurostimulator according to the invention has an enhanced ability to terminate epileptiform activity, is less likely to generalize ongoing epileptiform activity, optimally controls seizures by lowering the incidence of seizures as well as treating instances of breakthrough epileptiform activity, and provides for optimization of stimulation parameters programmed into the implanted neurostimulator.

DETAILED DESCRIPTION OF THE INVENTION

Figure 1:
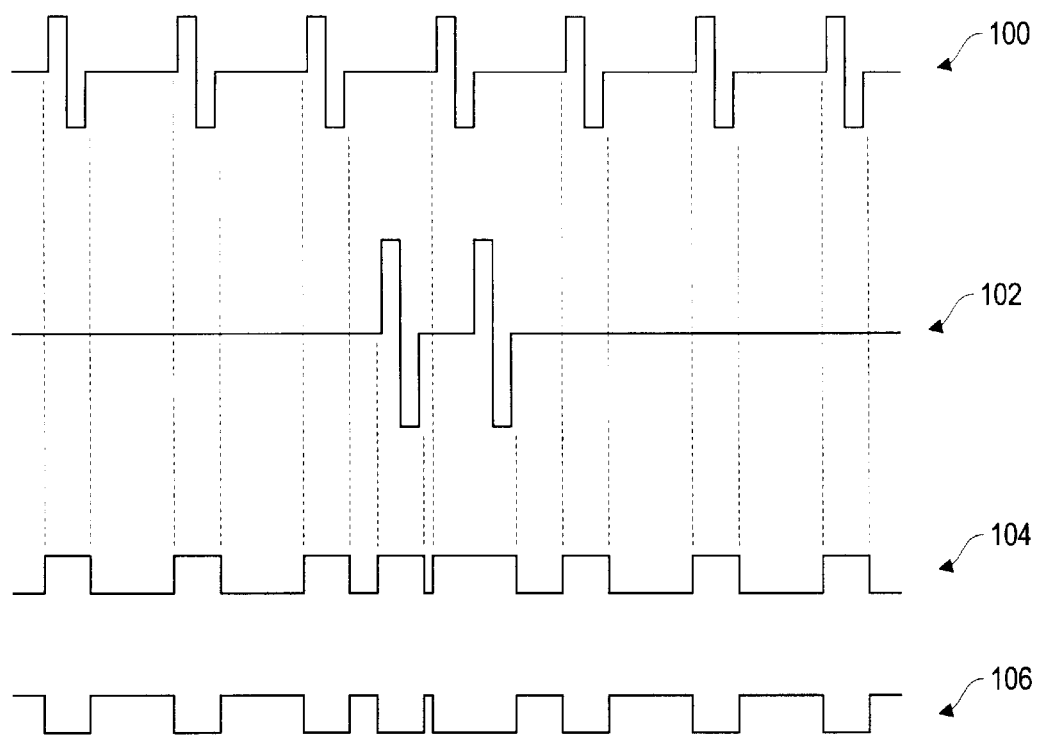
FIG. 1 shows a time graph representative of typical first and second modes and the operation of a blanking operation as used in an embodiment of the inventive process.

As noted elsewhere, this invention includes neurostimulation methods and devices for practicing that method.

Neurostimulation Methods

In one variation of the invention, the neurostimulation process includes at least two modes. The first mode involves application of a generally "non-responsive" electrical stimulation (or stimulation signal) to the brain. The second mode involves the application of a "responsive" electrical stimulation to the brain or a sensory stimulation elsewhere to the body. Optionally, the process includes steps for detection of electrical activity of the brain, analysis of that activity for impending or existent epileptiform activity, and decision-making steps relating whether to initiate responsive stimulation or to change the parameters of that stimulation.

As used herein, "non-responsive" stimulation refers to the application of electrical therapy intended to lower the probability of a seizure occuring. The parameters (electrode or electrodes used, morphology of the stimulating signal, number of pulses or cycles of the stimulating signal, amplitude, pulse to pulse interval or frequency of the stimulating signal, duration of the stimulating signal, etc.) of the non-responsive stimulation, or the application of the non-responsive stimulation may be set or varied as a result of the detection of signals from the patient's body including the nervous system and brain. The parameters of non-responsive stimulation may also be set by a physician. In general, however, and unless the context of the term indicates otherwise, a non-responsive stimulation is one in which the parameters of that stimulation are not controlled or modified in the implantable neurostimulator as a result of the detection of an existing or impending epileptiform event unless done so in conjunction with the use of the responsive stimulation.

As used herein, "responsive" stimulation refers to the application of electrical therapy in response to the detection of an electrographic (or some other) event indicating an impending or existent seizure. The electrographic event may be the beginning of an electrographic seizure, epileptiform activity, or other features of the EEG that typically occur prior to a seizure. Other events may include motion detection, or external triggering.

As used herein, "seizure" may represent a behavioral seizure wherein clinical evidence of functional or cognitive manifestations of the seizure may be elucidated by testing the patient; or electrographic seizure which refers to abnormalities detectable on the EEG (whether from brain, scalp or other electrodes, where internal EEGs are also known as ECoGs).

The term "epileptiform activity" refers to the manifestation on an EEG (cortical, depth, scalp or other electrodes, where internal EEGs are also known as ECoGs) of abnormal brain activity whether associated with clinical manifestations or not.

The term "stimulation" is used to refer to an electrical signal applied to brain tissue or some type of sensory input applied to the patient to elicit a response. The latter may include such physical motions such as vibration, other electrical signals not to brain tissue (for example somatosensory stimulation resulting in a scalp twitch or sensation in the scalp or other part of the body), light flashes, sound pulses, etc.

"Electrical stimulation" means the application of an electric field or electric current to biological tissue.

The brain's electrical activity is detected and analyzed to detect epileptiform activity or to detect such impending activity. If the epileptiform activity is present or impending, responsive stimulation (i.e. the second mode) may be initiated. The results of the analysis of the epileptiform activity may also be used to modify the parameters of the non-responsive stimulation to improve the suppression of seizures or other undesirable neurological events.

The parameters (electrode or electrodes used, morphology of the stimulating signal, number of pulses or cycles of the stimulating signal, amplitude, pulse to pulse interval or frequency of the stimulating signal, duration of the stimulating signal, etc.) of the responsive stimulation may be varied. The variation of the parameters may be based either upon a preprogrammed sequence or based upon some characteristic of the detected epileptiform activity. Additionally, the parameters of the responsive stimulation may be advantageously varied between different episodes of spontaneous epileptiform activity to minimize the tendency of the stimulation itself to predispose the brain to epileptogenesis (also known as "kindling"). Application of the responsive stimulation may be temporally paused or the amplifier blanked during responsive stimulation to allow analysis of the electrical activity of the brain to determine whether the stimulation has had its desired effect. Readjustment of the parameters of the responsive stimulation in the second mode may be repeated as long as it is advantageous in terminating the undesirable epileptiform activity.

This inventive procedure provides for multimodal therapies to be delivered not only to terminate impending or existent epileptiform activity, but also to diminish the likelihood that seizures will occur either due to the patient's underlying condition, or the possible epileptiogenicity of responsive therapy. In addition to providing for responsive stimulation delivered upon detecting an indication of epileptiform activity, this invention includes the additional first mode of operation for decreasing the incidence of seizures using non-responsive stimulation. The use of non-responsive stimulation in conjunction with responsive stimulation optimizes the control of seizures by providing a multimodal device that reduces the incidence of seizures, and is also effective at terminating any breakthrough seizures that may occur. The first mode of operation may also be used to reduce the potential epileptogenesis of the second mode, and may be scheduled based upon the use of the second (responsive) mode.

In addition, a testing mode is provided in the implanted device that can be used in conjunction with the responsive and non-responsive modes of operation mentioned above. Once the implantable neurostimulator has been connected to the patient, the testing mode allows for non-invasive verification of the functionality and appropriate programmed settings of the parameters for the responsive and non-responsive modes of operation.

Non-responsive Stimulation

In its most basic variation, the procedure and device provides neurostimulation in a first mode, non-responsive (i.e. programmed) stimulation, which is believed to modulate neurotransmitter levels or provide neural desynchronization in the brain resulting in a reduction of seizure incidence. Appropriate use of this non-responsive mode may also be used to reduce the risk of "kindling," a phenomenon whereby stimulation may make the neural tissue more prone to epileptogenesis. In addition, any epileptiform electrical activity that may occur is terminated by responsive stimulation in the second mode. As will be discussed below, the first mode (non-responsive) stimulation and the second mode (responsive) stimulation may be delivered from the same electrode, but also may be delivered from separate electrodes connected to the same implantable neurostimulator. The location of the electrode for the second mode (responsive) stimulation is preferably near the epileptogenic focus. The electrode location for the first mode (non-responsive) stimulation is often in a deep brain structure such as the thalamus, basal ganglia, hippocampus, or amygdala, or is in contact with the cerebellum, if it is not in the same location as the electrode for the second mode (responsive) stimulation.

The first mode (non-responsive) stimulation typically is made up of low intensity, short duration pulses delivered at about a 0.5 to 500 Hz rate. The pulses may be square pulses, or may have other morphologies such as triangular, trapezoidal or haversine to reduce the rate of change of intensity of the pulse. The pulses may be voltage controlled, or preferably, current controlled. In general the pulses will be biphasic to achieve charge balance, but waveforms having a net DC component may also have utility if used in conjunction with appropriate electrodes. To reduce the likelihood of responsive stimulation promoting epileptogenesis and to reduce the frequency of seizures, low frequency stimulation having a primary frequency of around 0.5 to 15.0 hertz (or pulse to pulse intervals of around 67 milliseconds to 2 seconds) may be used for typically 0.05 to 60 minutes or more delivered from the same electrode as the responsive stimulation, or from a different electrode. The low frequency stimulation may be delivered at a time related to completion of responsive stimulation, or on a scheduled basis. The parameters for application of the non-responsive stimulation may be varied according to circadian rhythms. In particular, for some patients, it will be advantageous to alter the stimulation patterns before or during normal sleep times to avoid disrupting sleep patterns, particularly REM sleep.

The characteristics of sinusoidal, quasi-sinusoidal, haversine, and other waveform morphologies will be described in greater detail below.

Responsive Stimulation

As noted above, the responsive stimulation is initiated when an analysis of the brain's electrical activity shows an impending or existent neurological event, such as epileptiform activity. To detect such activity reliably while the first (non-responsive) mode of stimulation is in progress often presents challenges. In some cases, the level of non-responsive stimulation is set at a low enough level, and the sensing electrodes are physically far enough away, that the stimulation does not interfere with detection of brain activity. The use of closely spaced electrodes for either non-responsive stimulation and detection, or both, is helpful in this regard. Often however, it is necessary to take measures to keep the non-responsive stimulation from interfering with detection of brain activity. One method for doing that is to "blank" the detection amplifier (or other detecting circuit component) during the pulse output of the non-responsive stimulation. If that is not effective in eliminating the interference, it may be necessary to periodically pause application of the pulsatile non-responsive stimulation to allow detection of brain activity. If the non-responsive stimulation is delivered as a substantially continuous waveform, particularly one that is largely sinusoidal, the use of notch filtering, interference filtering or other continuous time techniques may be used eliminate the non-responsive stimulation artifact from the amplifier used for detecting brain activity.

FIG. 1 shows the known concept of "blanking" in this inventive procedure. We show in the uppermost portion in the drawing a representative non-responsive stimulation signal 100 as a function of time. The pulse width of each stimulation pulse is exaggerated for clarity. In practice, a typical pulse width of 0.2 milliseconds could be used, and the pulse-to-pulse interval would be about 20 milliseconds. Similarly, just below the non-responsive stimulation signal 100 is a representative responsive stimulation signal 102 that has been initiated as the result of detected electrical neurological activity. During the period just before and during each of the stimuli, both responsive and non-responsive, the input to some component of the detecting function, typically an amplifier, is "blanked" to prevent detecting the stimuli as if they were signals generated by the brain. The blanking is terminated a short period after the pulse ceases. For instance, although the entire stimulation pulse duration is about 0.2 milliseconds, the entire blanking period per pulse might be about 1.0 millisecond. For a pulse-to-pulse interval of 20 milliseconds, 95% of the time remains available for detecting brain activity. The blanking signal 104 shows the gating time (not to scale), which is used to prevent the sensors from passing information to the related sensing, and detecting equipment during the time the stimulation is imposed. The blanking signal curve 104 shows the "on-off" states for the blanking. The dashed lines from the non-responsive stimulation signal 100 and the responsive stimulation signal 102 depict how the blanking periods are formed.

The typical stimulation pulses shown in FIG. 1 are biphasic and typically have a duration of 0.025 to 0.50 milliseconds per phase. The blanking signal 104 slightly precedes and lasts longer than the stimulation pulses to assure that no stimulation artifact disturbs the measurement. The overall duration of the blanking time desirably is typically 1 to 5 milliseconds. A measurement enable signal 106 is the inverse of the blanking signal 104, and represents the time when the detection functions of a neurostimulator according to the invention can be enabled.

Figure 2:
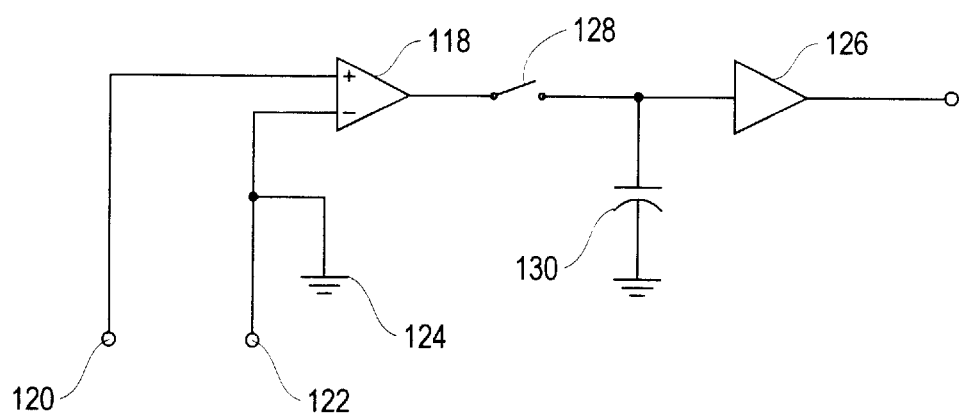
FIG. 2 shows an exemplary circuit useful in blanking an input to a measurement step as shown in FIG. 1.

FIG. 2 shows a block diagram of a circuit that may be used to cause blanking as shown in FIG. 1. A differential amplifier stage 118 used to detect brain activity has two input electrodes 120 and 122. One of the electrodes 122 may be connected to a ground reference 124, which ground reference 124 may be either in the brain or elsewhere in or on the patient's body. The electrical signal received from the brain is amplified by the differential amplifier stage 118 before getting additional filtering and amplification by a secondary amplifier stage 126. When stimulation is not occurring, a blanking switch 128 interposed between the differential amplifier stage 118 and the secondary amplifier stage 126 is usually closed, allowing the signal from the brain to be amplified and filtered. During stimulation, the blanking switch 128 is momentarily opened to keep electrical artifacts from the various stimulation pulses from corrupting the output of the secondary amplifier stage 126. When the blanking switch 128 is opened, a capacitor 130 keeps the input of the secondary amplifier stage 126 stable in a "track-and-hold" fashion until blanking switch 128 is closed. In some cases it may be advantageous to add gain reduction to the first amplifier stage and/or auto-zeroing to further minimize the effect of transients caused by stimulation.

Alternatively, if narrow-band stimulation waveforms are employed (such as sine waves or quasi-sinusoidal signals) a technique known as interference filtering may be used advantageously to remove stimulation artifacts from the electrical brain signal being sensed. Since there is complete knowledge of the interfering signal (i.e. the stimulation waveform), a portion of it may be fed into the inverting input of an error amplifier along with the brain signal. If the phase and amplitude of the interfering signal is correctly adjusted, it will completely cancel out the stimulation artifact in the brain signal being sensed. The phase and amplitude may be set ahead of time for very stable systems, or a feedback mechanism can be used to drive the energy of the interfering signal towards zero. This technique has advantages over an alternative approach to artifact removal, notch filtering, in that it is not subject to ringing, and it results in minimal distortion of the underlying signal being sensed. Furthermore, the technique is inherently adaptive as the frequency content of the stimulation signal is varied, which is difficult to do with tracking notch filters. However, it is anticipated that there are occasions where conventional notch filtering may be used to remove narrow band stimulation signals from the brain activity being sensed.

Figure 3:
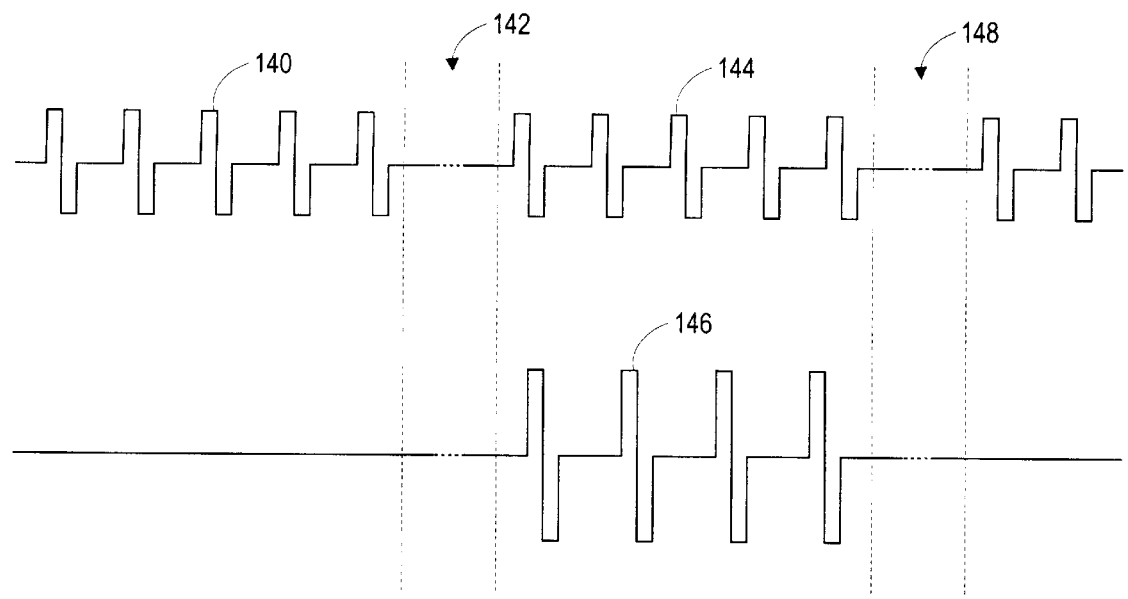
FIG. 3 shows a time graph representative of signals employed in a first method for detecting electrical activity in the brain by pausing the responsive and non-responsive stimulation of the inventive process.
Figure 4:
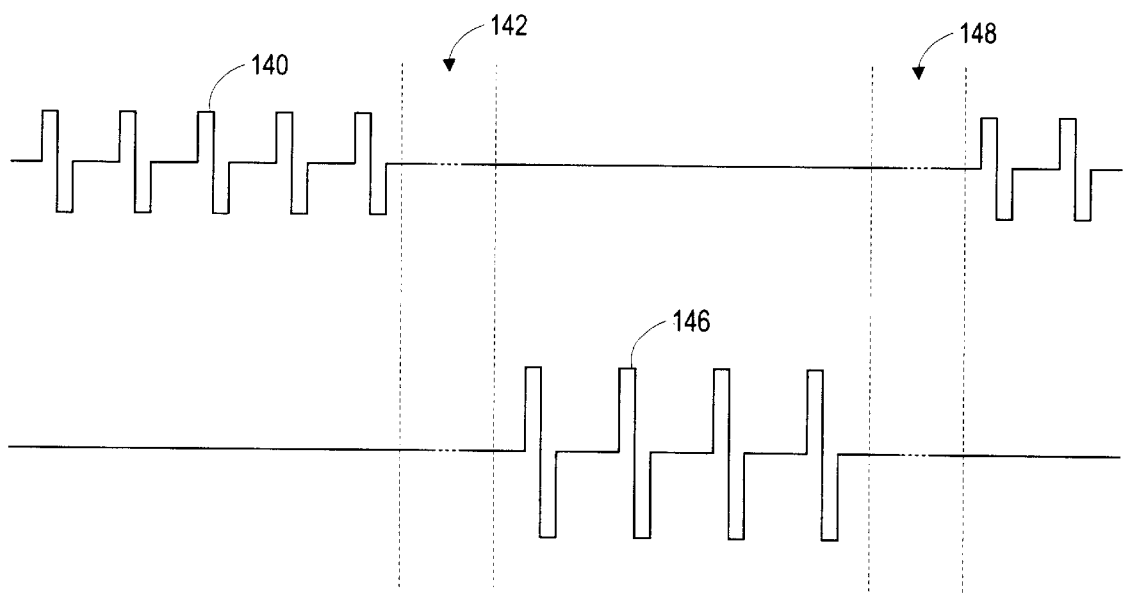
FIG. 4 shows a time graph representative of signals employed in a second method for detecting electrical activity in the brain by pausing the responsive and non-responsive stimulation of the inventive process.

As noted above, another variation of the step for detecting the electrical activity of the brain amidst intermittent instances of stimulation is depicted in FIGS. 3 and 4. In this variation, instead of blanking the input to the amplifier, the various electrical stimulation signals are paused or stopped for a discrete period, during which the measurement of neuroelectrical activity may be made.

FIG. 3 shows a situation in which a non-responsive stimulation signal 140 (shown here with an exaggerated pulse width for clarity) has been applied to the patient and continues to a first quiet or quiescent period 142 during which monitoring of brain electrical activity is performed. In this variation, whether or not epileptiform activity is found to be approaching or existent during this initial monitoring period 142, the non-responsive stimulation signal 140 is restarted 144.

In any event, returning to the first variation shown in FIG. 3, in this example, pending or existent epileptiform electrical activity is detected in some part of the brain during the initial monitoring period 142 and the responsive stimulation 146 is initiated. In the disclosed embodiment, the non-responsive stimulation 144 continues. Later, both the non-responsive stimulation 144 and the responsive stimulation 146 are then temporally paused for monitoring during a subsequent monitoring period 148 to determine whether epileptiform activity has ceased. The responsive stimulation 146 and non-responsive stimulation 144 may be paused simultaneously, or one may cease before the other. In the instance depicted in FIG. 3, the epileptiform activity is terminated and the responsive stimulation 146 is not re-initiated after the subsequent monitoring period 148. Of course, as is discussed below, the responsive stimulation 146 is re-initiated; it may be re-initiated either with or without being modified in some fashion.

There are several methods of predicting an impending seizure. For example, an analysis of long-term EEG signal energy may provide indications of an impending seizure up to several hours before the seizure itself is clinically manifested or apparent in EEG analysis. In particular, accumulated energy may indicate an impending seizure five or more minutes before its electrographic onset, and long-term energy bursts may be predictive of a seizure six or more hours before its onset. See, e.g., Litt et al., "Epileptic Seizures May Begin Hours in Advance of Clinical Onset: A Report of Five Patients," Neuron, 30: 51–64 (April 2001). Other prediction schemes are possible. Under such circumstances, the inventive neurostimulation process may both modify the non-responsive parameters of stimulation and initiate the stimulation. The stimulation changes the underlying dynamics of the brain, resulting in a reduced likelihood of the impending seizure occurring. In this event, largely continuous waveforms (sinusoidal or quasi-sinusoidal) at relatively low frequencies (0.25 to 10 Hz) are preferred. Of course, if a seizure occurs, or if the monitoring scheme determines that a seizure is immediately imminent, the responsive mode of stimulation may be applied automatically to terminate it.

FIG. 4 shows essentially the same scheme as that shown in FIG. 3 with the major exception that the variation found in FIG. 4 eliminates the non-responsive stimulation signal 144 (FIG. 3) after the initial monitoring period 142. This variation can be determined either by the decision-making devices of this invention or by pre-programming.

Figure 5:
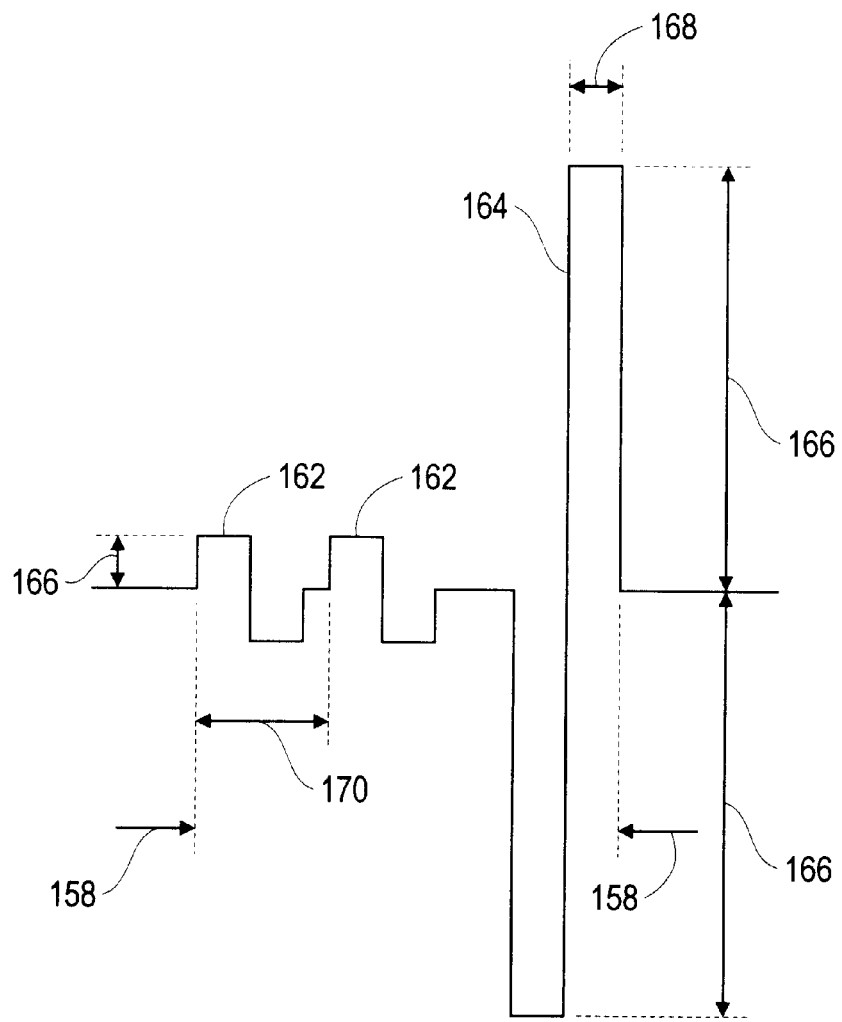
FIG. 5 shows a graph setting forth terminology and conventions used herein to describe pulse and burst parameters in a stimulation waveform according to the invention.

The second electrical stimulation signals in each of FIGS. 1, 3, and 4 are depicted as trains of biphasic pulses. FIG. 5 illustrates the terminology conventions used in discussing those signals.

In FIG. 5 is shown a burst 158 of three pulses 160, 162, and 164. The first two pulses 160 and 162 are of low amplitude—the term "amplitude" 166 and the physical meaning may be seen in FIG. 5. Amplitude may refer to peak amplitude or average amplitude for non-square pulses. It may refer to any phase of a pulse if the pulse is multiphasic. Amplitude may also be used to describe either the voltage or current for an electrical pulse. The "pulse duration" 168 (also known as the width or time-length of the pulse) is depicted as well. Finally, the "pulse-to-pulse interval" 170 (also referred to as the inter-pulse interval) of the pulses is the time between the beginnings of consecutive pulses.

As noted above, it is within the scope of this invention to vary the electrode used and the parameters of the pulses or of the burst, as shown in FIG. 5, for both the responsive and non-responsive modes of stimulation.

FIGS. 6–11 show a number of variations of the pulse and burst makeup, which pulse and parameters may be varied either during a responsive electrical stimulation or may be varied from burst to burst.

Figure 6:
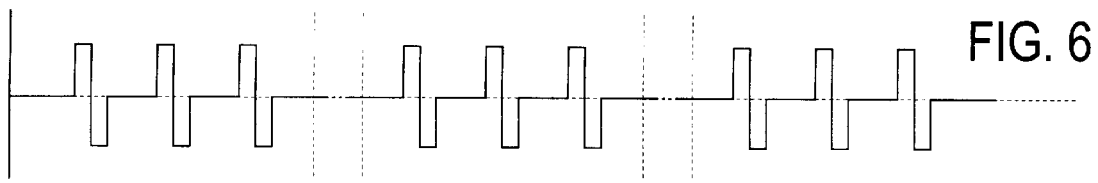
FIG. 6 shows a waveform graph of an exemplary pulse pattern with constant amplitude and duration employed according to an embodiment of the invention.

FIG. 6 shows a simple sequence of bursts having pulses of the same frequency and amplitude in each pulse.

Figure 7:
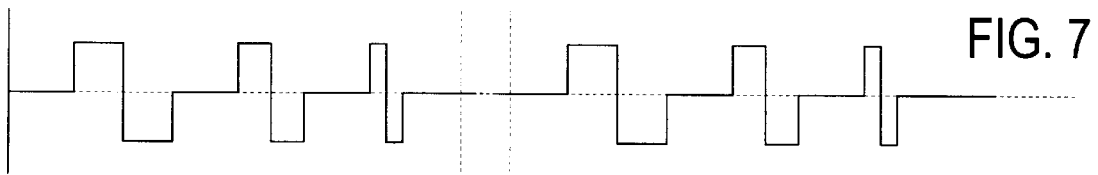
FIG. 7 shows a waveform graph of an exemplary pulse pattern with constant amplitude and varying durations employed according to an embodiment of the invention.

FIG. 7 shows a burst of three pulses in which the duration of the pulses varies as a function of time.

Figure 8:
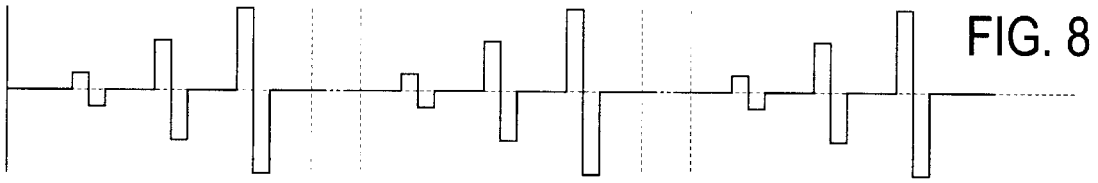
FIG. 8 shows a waveform graph of an exemplary pulse pattern with constant duration and varying amplitudes employed according to an embodiment of the invention.

FIG. 8 shows a pair of bursts in which the amplitude of the pulses varies during each burst.

Figure 9:
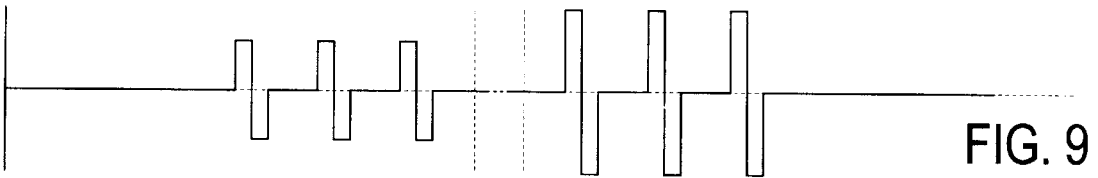
FIG. 9 shows a waveform graph of an exemplary pulse pattern with constant duration and varying burst amplitudes employed according to an embodiment of the invention.

FIG. 9 shows a pair of bursts in which the amplitude of the pulses is increased during the second pulse.

Figure 10:
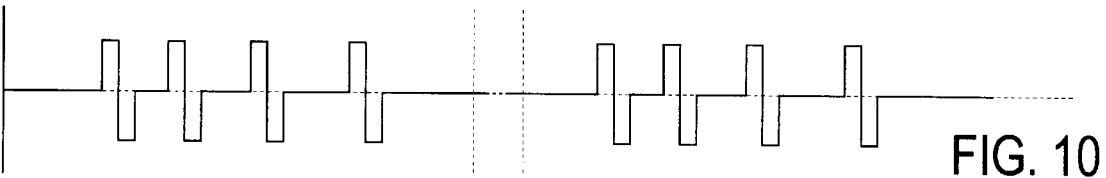
FIG. 10 shows a waveform graph of an exemplary pulse pattern with varying interpulse intervals employed according to an embodiment of the invention.

FIG. 10 shows a variation in which the pulse-to-pulse interval is varied within a burst. This variation is desirable in de-synchronizing neuronal activity. The range of pulse-to-pulse intervals may be varied randomly (or pseudo-randomly) or changed in a systematic fashion, such as incrementing or decrementing the pulse-to-pulse interval within a burst.

Figure 11:
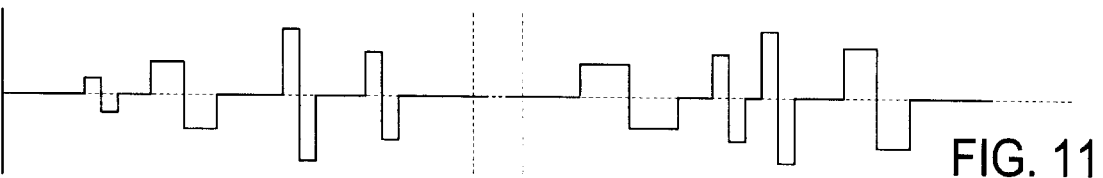
FIG. 11 shows a waveform graph of an exemplary pulse pattern with varying amplitudes and durations employed according to an embodiment of the invention.

FIG. 11 depicts another variation of the invention that desynchronizes brain activity to terminate epileptiform activity by spatially desynchronizing activity in the vicinity of the stimulation electrode. To accomplish this, various individual pulse parameters, e.g., pulse spacing, duration or width, and amplitude, within a burst may be varied, particularly in a random, pseudo-random, or fractal fashion. Shorter duration pulses (on the order of 50 to 150 microseconds) tend to directly depolarize smaller diameter nerve cells. Longer pulses (100 to 500 microseconds) tend to depolarize larger diameter nerve cells. By varying pulse amplitude, the individual pulses may be tailored directly to depolarize different neural tissue. Lower amplitude pulses directly depolarize tissue in the immediate vicinity of the electrode; higher amplitude pulses directly depolarize tissue both near the electrode and at some distance from the electrode. By varying the amplitude of the pulses within a burst, local tissue can be depolarized at a higher rate than tissue somewhat distant from the electrode.

Since the tissue disposed near an electrode may have highly variable anatomy, it is anticipated that any or all of the parameters described (pulse to pulse interval, pulse amplitude, the use of hyperpolarizing pulses, pulse width, etc.) may be varied alone or in combination to optimize the ability of a burst to terminate epileptiform activity in the brain while improving the safety of the burst by reducing the likelihood of inducing epileptiform activity or generalizing such pre-existing activity.

In addition to producing bursts having pulse intervals having pre-set or absolute time increments, this inventive procedure includes the improvement of setting the pulse to pulse interval based upon the detected temporal interval of the epileptiform activity as sensed by the electrodes detecting the brain electrical activity. In this mode of operation, the rate of the sensed epileptiform activity is detected and measured. The rate of the detected activity is used to modulate the rate, or the average rate, of the burst used to terminate the epileptiform activity perhaps as depicted in FIG. 11.

It is desirable to synchronize initiation of a responsive stimulation burst with certain parameters of the sensed EEG. As is described with greater particularity in U.S. patent application Ser. No. 09/543,264 to Pless, filed on Apr. 5, 2000 and entitled "A Neurostimulator Involving Stimulation Strategies and Process for Using It" (the entirety of which is incorporated by reference), the initiation of the responsive stimulation burst may be delayed for a calculated period that varies from 0 to 100% of the detected EEG interval.

For the purposes of this invention, a burst (in this variation and in each of the others described herein) may be any number of pulses, but typically is in the range from 1 to 100 or more pulses. After the burst is delivered, the EEG is re-examined, and if the epileptiform activity was not terminated, a subsequent burst may automatically be delivered. As was the case above, the subsequent burst may have the same signal parameters as the first burst, may re-adapt to the changing EEG rate, or may have new parameters to more aggressively attempt to terminate the epileptiform activity, e.g., higher pulse or burst rate, more pulses, higher amplitude, or modified pulse to pulse intervals, variations on such parameters are shown in FIGS. 6 through 11.

Figure 12:
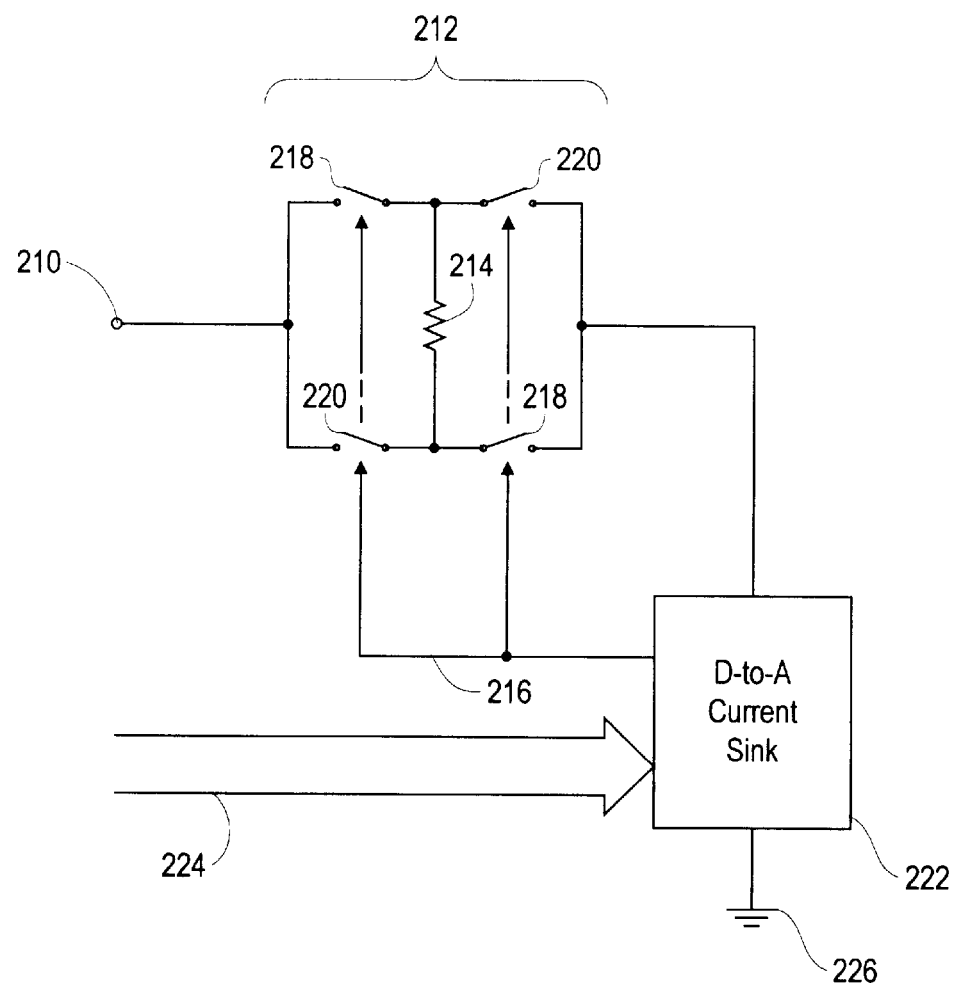
FIG. 12 is a simplified schematic diagram of a bipolar programmable current source employed in an embodiment of the invention.

FIG. 12 is a conceptual representation of exemplary stimulation circuitry usable for both non-responsive and responsive stimulation according to the invention. A relatively high and substantially stable compliance voltage is applied to an input 210. In conjunction with the other aspects of FIG. 12, the compliance voltage acts as an analog stimulation signal, which is passed to an H-bridge circuit 212, causing current to flow through the attached load 214 (i.e., the patient's tissue being stimulated) in one direction or the other, depending on the state of a switching signal 216. Accordingly, in one state, the switching signal 216 causes a first pair of switches 218 in the H-bridge 212 to close and a second pair of switches 220 to open, causing current to flow through the load 214 in a first direction, and in its other state, the switching signal 216 causes the first pair of switches 218 to open and the second pair 220 to close, causing current to flow through the load 214 in the other direction.

The magnitude of the current flowing through the load 214 is controlled by a D-to-A current sink 222. The D-to-A current sink 222 also provides the switching signal 216 that controls the direction of the current flowing through the load 214. The D-to-A current sink 222 is driven by a digital data bus 224 (typically five bits, as described above), which receives data from a microcontroller or other central processing unit, a clocked memory, or some other generator of digital data, either general-purpose or special-purpose, hardware or software. The current sink 222 receives digital data presented on the bus 224 and controls the current flowing from the compliance voltage input 210, through the H-bridge 212 and the load 214, and into the sink 222 and finally a ground 226 as described in additional detail below. By allowing current to pass through the patient load 214 in either direction, the H-bridge circuit 212 allows the essentially monopolar compliance voltage input 210 and D-to-A current sink 212 to provide a bipolar stimulation signal to the patient load 214.

In addition to being able to make arbitrary waveforms, another advantage of the circuit configuration of FIG. 12 is that it is possible to produce balanced outputs without needing critically matched components. Typical requirements for a useful A to D converter would be a 5 bit converter having 0.5 mA current steps up to a full range of 15 mA with a 15 volt compliance voltage, although other values could also be used.

Figure 13:
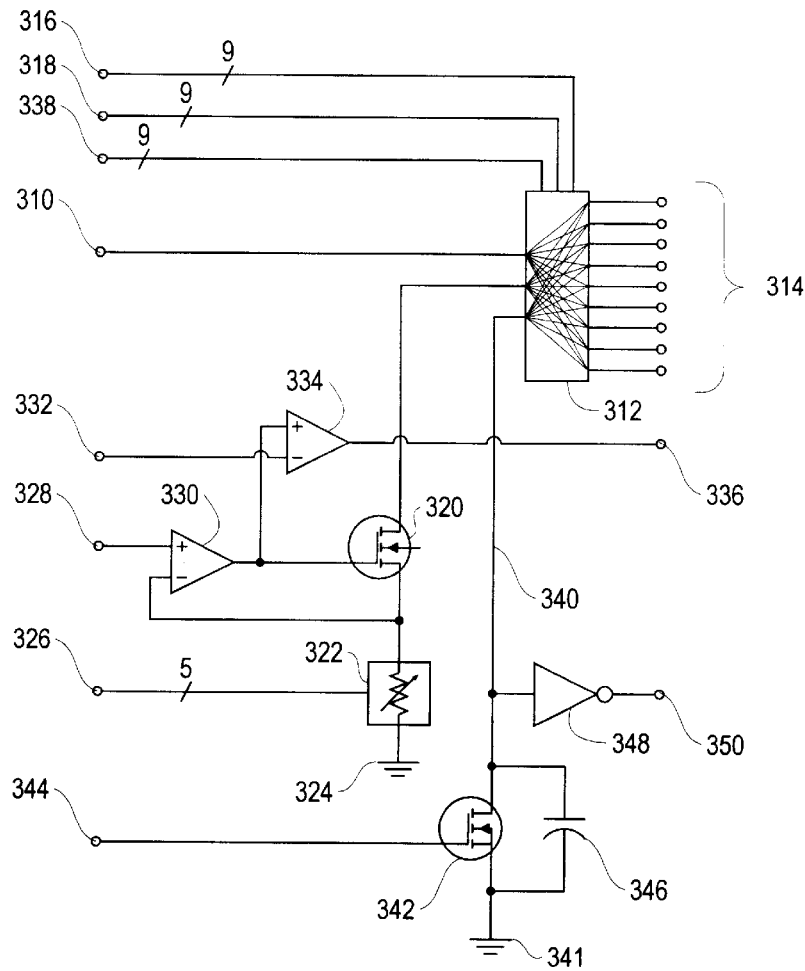
FIG. 13 is a schematic diagram of a stimulation current source with current tilt detection and current leakage detection and prevention capabilities according to an embodiment of the invention.

The concept set forth above and illustrated in FIG. 12 is preferably implemented as a controlled-current stimulation signal generator as depicted in FIG. 13. A substantially constant compliance voltage is applied to a stimulation signal input 310. In the disclosed embodiment of the invention, the compliance voltage is the minimum voltage necessary to achieve a maximum desired current of 15 mA through a load having an impedance below approximately 1.0 kΩ, or as described herein, approximately 15 volts. If the impedance is higher than 1.0 kΩ, currents lower than 15 mA are generally still achievable. In an implantable device, this compliance voltage would generally be achieved by charging a stimulation signal storage capacitor with a DC-to-DC converter operating from a substantially lower battery voltage.

In operation, the compliance voltage at the stimulation signal input 310 is applied through a switching matrix 312 to one or more stimulation electrodes chosen from a set of electrodes 314 via a stimulation electrode selection bus 316, and returned via different return electrodes chosen from the electrodes 314 via a return electrode selection bus 318, and through the switching matrix 312. To accomplish the H-bridge functionality described above with reference to FIG. 12, the stimulation electrodes and the return electrodes are reversed in the matrix 312 (by switching the data on the stimulation electrode selection bus 316 and the return electrode selection bus 318), thereby reversing the current flow when desired.

After passing through the patient, the current originating from the stimulation signal input 310 passes through a current control FET 320, into a programmable resistor 322, and into a ground 324. The resistance of the programmable resistor 322 is controlled by a five-bit digital data bus 326, and in connection with a current control reference voltage 328 and a current control op amp 330, modulates the current flowing through the programmable resistor 322, and hence, the current flowing through the patient connected via the electrodes 314.

A constant and precise current control reference voltage 328 (which, in the disclosed embodiment of the invention, is trimmable to compensate for component tolerances, particularly in the programmable resistor 322) is applied to the positive input of the current control op amp 330, and the negative input of the op amp 330 is connected to the upstream end of the programmable resistor 322. Because the op amp 330 will control its output to maintain the two inputs at the same potential, the op amp 330 will cause the voltage present at the upstream end of the programmable resistor 322 to match the reference voltage 328 by actuating the current control FET 320 as necessary. Accordingly, as the voltage present at the upstream end of the programmable resistor 322 is known and constant, the current passing through the programmable resistor 322 can be accurately modulated by controlling the resistance of the programmable resistor 322. Consequently, together, the op amp 330, the FET 320, and the programmable resistor 322 make up a programmable current digital-to-analog converter.

As the path from the stimulation signal input 310, through the switching matrix 312, through the patient via stimulation and return electrodes (chosen from the electrodes 314), returning through the switching matrix 312, and passing through the current control FET 320 and the programmable resistor 322 and into ground represents a single circuit and current path, the current flowing through the patient must be the same as the current flowing through the programmable resistor 322. In this manner, precise and accurate stimulation current control is achieved by a system according to the invention. If stimulation times are also controlled, the total charge (and hence the average charge density, which is dependent on electrode surface area) will also be controlled.

Figure 14:
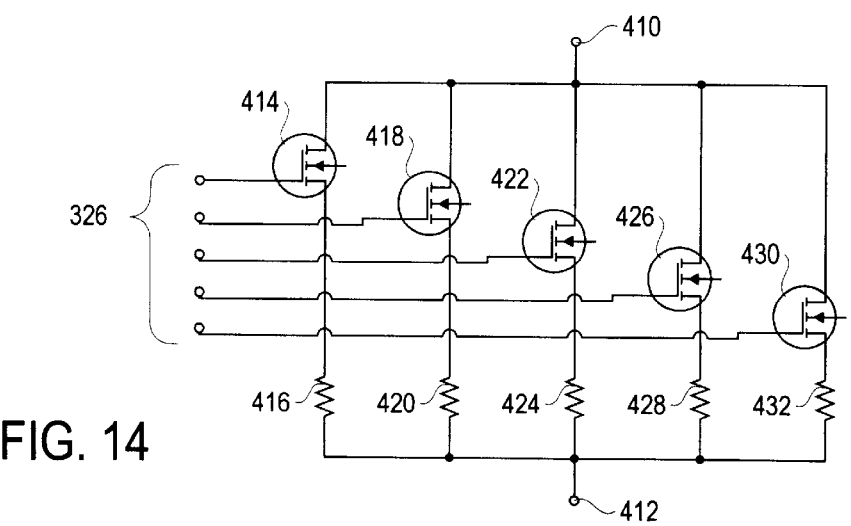
FIG. 14 is a schematic diagram of a resistive digital-to-analog converter usable in conjunction with the stimulation current source of FIG. 13.

An exemplary implementation of the programmable resistor 322 is illustrated in FIG. 14. As shown, current flows through the programmable resistor 322 from an upstream input 410 to a downstream output 412. Between the input 410 and the output 412, a plurality of parallel resistances and switching FETs are interposed and separately controllable by individual bits of the five-bit digital data bus 326.

The least-significant bit of the digital data bus 326 controls a first switching FET 414, which when actuated allows current to pass between the input 410 and the output 412 through the first FET 414 and a first resistor 416. The series resistance of the first resistor 416 and the "on" resistance of the first FET 414 should equal a known quantity, which in the disclosed embodiment is 1.0 kΩ. The "off" resistance of the first FET 414 is very high, and an insignificant amount of current will pass through it when it is not actuated.

Similarly, the second-least-significant bit of the digital data bus 326 controls a second switching FET 418, which when actuated allows current to pass between the input 410 and the output 412 through the second FET 418 and a second resistor 420. The series resistance of the second resistor 420 and the "on" resistance of the second FET 418 should equal half of the known quantity, or 500 Ω. Accordingly, when the second FET 418 is actuated, twice the current should pass through the programmable resistor 322 as when the first FET 414 is actuated (assuming a constant voltage, as set forth in FIG. 13 above). If both the first FET 414 and the second FET 418 are actuated, three times the current should pass through the programmable resistor 322 as when only the first FET 414 is actuated.

Similarly, the higher-order bits of the digital data bus 326 control a third FET 422, a fourth FET 426, and a fifth FET 430, which respectively control the current flowing through a third resistor 424, a fourth resistor 428, and a fifth resistor 430. The values of the third, fourth, and fifth resistors should selected such that their resistance in series with the corresponding FETs are equal to ¼, ⅛, and ¹⁄₁₆ of the known quantity, respectively. To accomplish this, it may necessary to couple multiple FETs in parallel (thereby reducing their cumulative "on" resistance). In the disclosed embodiment, it is also preferable to employ multiple resistors (each having the same resistance value) in parallel to accomplish the fractional ½, ¼, ⅛, and ⅙ resistance values, as greater relative precision is generally achieved by doing so.

Together, the five FETs and resistors illustrated in FIG. 14 make up a programmable resistor with five-bit (and thirty-two level) resolution; and when coupled to the current control of FIG. 13, the FETs and resistors allow precisely variable currents to be applied to a patient.

As the programmable resistor 322 of FIG. 14 is connected in series with the load 214 (FIG. 12) provided by the patient's tissue being stimulated, the currents flowing through the programmable resistor 322 and the load 214 are necessarily equal (in the absence of any leakage or parallel circuit elements). Accordingly, it should be noted that while the disclosed embodiment of the invention calls for the load 214 to be situated first, between the stimulation signal input 310 (FIG. 13) and the programmable resistor 322, alternative arrangements (e.g., a reversal of the programmable resistor 322 and the load 214) are possible and would be equally useful in a system according to the invention.

Returning to the details of FIG. 13, several other features are present and operate in connection with the controlled current source described above. In particular, if the compliance voltage at the stimulation signal input 310 to too low to accommodate a stimulation current selected by the programmable resistor 322, the current control op amp 330 will immediately increase the potential applied to the gate of the current control FET 320, in an attempt to decrease the voltage drop across the FET 320 and increase the voltage at the upstream end of the programmable resistor 322 (and hence the current flowing through the programmable resistor 322). If the increase in potential causes the op amp 330 to go to its positive rail (as it will almost immediately if the compliance voltage is insufficient), and the potential exceeds a preset current tilt threshold voltage 332 (set to be slightly below the maximum output voltage of the op amp 330), a comparator 334 will trigger and cause a tilt output 336 to be actuated. A system according to the invention can respond to the tilt output 336 to terminate stimulation, adjust stimulation currents, recharge the capacitor providing the compliance voltage, or take any other desired action to avoid injuring the patient or otherwise malfunctioning.

Moreover, when stimulation is not occurring, a third path through the switching matrix 312 controlled by a sense reference selection bus 338 allows one or more of the electrodes 314 to be coupled to a patient ground reference 340, which is used for sensing by an implantable neurostimulator according to the invention. The patient ground reference is coupled to a system ground 341 through a leakage detection FET 342 (which is biased by a leakage current bias 344 to have a threshold, or knee, at 7.5 µA) and a parallel capacitor 346. Any current flowing from the patient ground 340 to system ground 341 is generally indicative of current leakage from the stimulation capability of the neurostimulator through the electrodes 314.

Accordingly, when leakage current is below the threshold of the FET 342 and within the normal range, current flows through the FET 342 to system ground 341. If current increases above the threshold, the non-linear characteristics of the FET 342 cause the voltage drop across the FET 342 to increase, and patient ground 340 will be significantly higher in potential than system ground 341. This potential will serve to isolate patient ground 340 from system ground 341, thereby decreasing leakage, and simultaneously cause an inverter 348 to trigger and provide a signal to a leakage detection output 350, thereby providing a signal indicating that leakage is occurring. The capacitor 346 coupling the patient ground 340 to the system ground 341 serves at least two purposes—to AC-couple patient ground 340 to system ground 341, ensuring that patient ground 340 is effectively equivalent to system ground 341 in the frequency range used for sensing neurological events, and also to prevent short transients from triggering the leakage detection. The leakage detection output 350 may be used by a neurostimulator according to the invention to terminate stimulation, go into an inactive mode, discharge the capacitor providing the compliance voltage, or take any other desired action to avoid injuring the patient or otherwise malfunctioning. Preferably, when leakage is detected, all electrodes are shorted to ground, thereby shunting any leakage current away from the patient.

Figure 15:
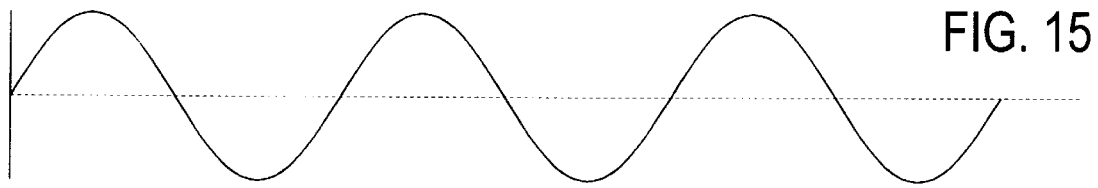
FIG. 15 is a graph of an exemplary sinusoidal stimulation waveform for use in accordance with an embodiment of the invention.

FIG. 15 shows a sinusoidal stimulation signal that can be produced and used for non-responsive or responsive brain stimulation according to the invention. In general, sinusoidal and quasi-sinusoidal waveforms are delivered at low frequencies to decrease the likelihood of seizures beginning, where low frequencies are 0.5 to 10 Hz delivered for 0.05 to 60 minutes at a time. Such waveform may be applied as a result of determining that a seizure has a higher probability of occurring than usual (prediction), on a scheduled basis, or after responsive stimulation has been applied to terminate epileptiform activity. Higher frequency sinusoidal or quasi-sinusoidal waveforms may be used to in responsive stimulation to terminate epileptiform activity. Amplitudes in the range of 0.1 to 10 mA would typically be used, but attention to safe charge densities is important to avoid neural tissue damage (where a conservative limit is 25 $\mu C/cm^2$ per phase).

Figure 16:
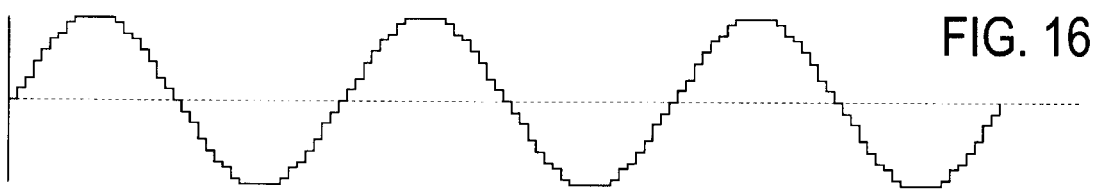
FIG. 16 is a graph of an exemplary stepwise approximation to the sinusoidal stimulation waveform of FIG. 15 for use in accordance with an embodiment of the invention.

In reality, the sinusoidal and quasi-sinusoidal waveforms presented herein would be constructed using the system depicted in FIGS. 12–14. As a result, the sinusoid of FIG. 15 is really generated as a stepwise approximation, via a series of small steps as shown in FIG. 16. The time between steps is dependent upon the details of the waveform being generated, but an interval of 40 microseconds has been found to be a useful value. It is anticipated that the stair step waveform of FIG. 16 may be filtered to arrive at a waveform more similar to FIG. 15, which would allow for longer periods of time between steps and larger steps. Likewise, for the waveforms of FIGS. 17–20 (described below), it is assumed that they may be created with a series of steps notwithstanding their continuous appearance in the figures.

Figure 17:
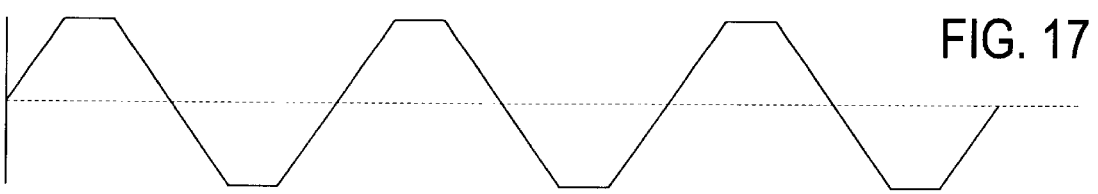
FIG. 17 is a graph of an exemplary trapezoidal approximation to the sinusoidal stimulation waveform of FIG. 15 for use in accordance with an embodiment of the invention.

FIG. 17 depicts a truncated ramp waveform where the rate of the ramp, the amplitude reached and the dwell at the extrema are all selectable parameters. The truncated ramp has the advantage of ease of generation while providing the physiological benefits of a sinusoidal or quasi-sinusoidal waveform.

Figure 18:
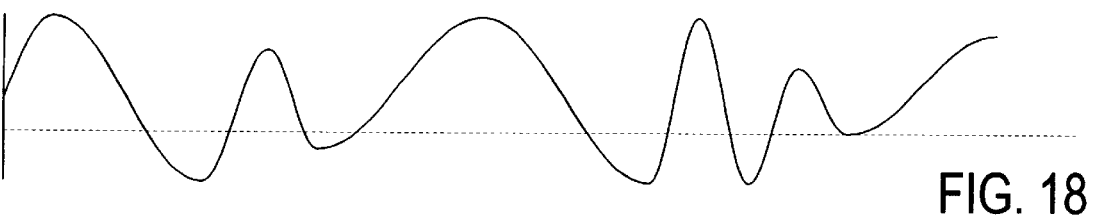
FIG. 18 is a graph of an exemplary sinusoidal stimulation waveform, with varying amplitude and frequency parameters, for use in accordance with an embodiment of the invention.

FIG. 18 shows a sinusoidal waveform where the amplitude and frequency are varied while the waveform is applied. The rate and amplitude of the variation may be varied based upon a predefined plan, or may be the result of the implanted neurostimulator sensing signals from the brain during application or between applications of the waveform, and adjusting to achieve a particular change in the sensed signals. The waveform of FIG. 18 is illustrated herein as having a positive direct current component, but it should be noted that this waveform, as well as any of the others described herein as suitable for use according to the invention, may or may not be provided with a direct current component as clinically desired.

Figure 19:
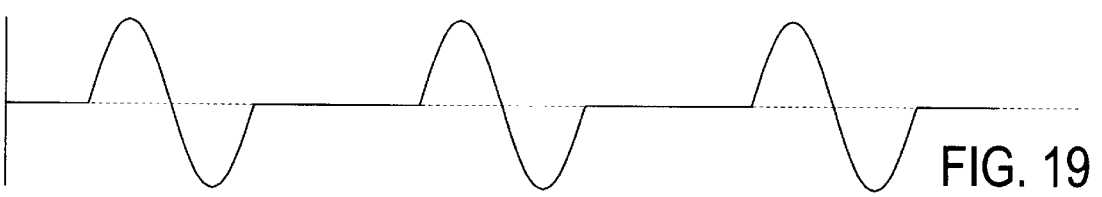
FIG. 19 is a graph of an exemplary stream of sinusoidal pulses for use in accordance with an embodiment of the invention.
Figure 20:
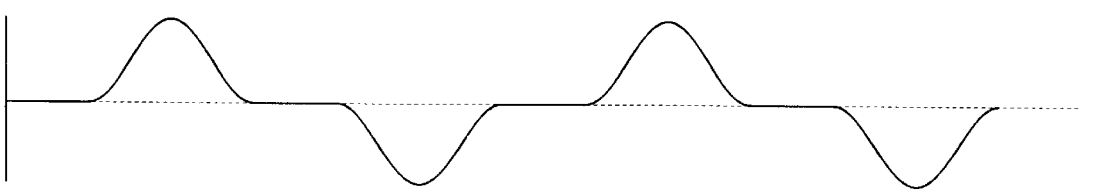
FIG. 20 is a graph of an exemplary stream of haversinusoidal pulses for use in accordance with an embodiment of the invention.

FIGS. 19–20 depict a variation where the stimulating waveform is generated having a largely smooth waveform, but having the additional feature where the interval between waveforms is set by varying a selectable delay, as would be used with the square pulse waveforms described previously. In FIG. 19, the stimulating waveforms are segments of a sine wave separated in time (of course the same technique could be used for the truncated ramp, or other arbitrary morphologies). FIG. 20 shows a variation where the derivative in time of the waveform approaches zero as the amplitude approaches zero. The particular waveform shown in FIG. 20 is known as a haversine pulse.

Although the term "haversine pulse" is useful to describe the waveform of FIG. 20, it should be noted that all of the waveforms represented in FIGS. 15–20 are considered herein to be generally "non-pulsatile," in contrast with waveforms made up of traditional discontinuous (e.g. square) pulses, examples of which are illustrated in FIGS. 6–11. As the term is used herein, "non-pulsatile" can also be applied to other continuous, semi-continuous, discontinuous, or stepwise approximated waveforms that are not exclusively defined by monophasic or biphasic square pulses.

Another advantage of the brain stimulation device described by FIGS. 12–14 is the ability to produce waveforms having a controlled direct current component (as illustrated in FIG. 18). This is not possible in known and existing devices having capacitive coupled outputs or active feedback circuits to simulate capacitive coupling. See U.S. Pat. No. 6,035,237 to Schulman et al. for examples. While capacitive coupling may improve safety in that a malfunctioning device would not be able to apply a direct current to neural tissue, it also decreases such a device's flexibility. Although care must be used in applying waveforms having direct current outputs (since tissue damage may result with direct currents), there is evidence that direct currents may be particularly effective in desynchronizing brain activity. See, e.g., Weiss et al., "Quenching Revisited: Low Level Direct Current Inhibits Amygdala-Kindled Seizures," *Experimental Neurology*, 154: 185–192 (1988); and Gluckman et al., "Electric Field Suppression of Epileptiform Activity in Hippocampal Slices," *Journal of Neurophysiology*, 76(6): 4202–4205 (December 1996).

In the disclosed embodiment, the default stimulation behavior provided by a neurostimulator according to the invention is to stimulate with charge-balanced biphasic pulses (as in the stimulation signals represented in FIGS. 6–11). This behavior is enforced by stimulation generation hardware that automatically generates a symmetric equal-current and equal-duration but opposite-polarity pulse as part of every stimulation pulse; the precise current control enabled by the present invention makes this approach possible. However, the neurostimulator is preferably programmable to disable the automatic charge balancing pulse, thereby enabling the application of monophasic pulses (of either polarity) and other unbalanced signals.

Alternatively, if desired, charge balancing can be accomplished in software by programming the neurostimulator to specifically generate balancing pulses or signals of opposite phase. Regardless of whether charge balancing is accomplished through hardware or software, it is not necessary for each individual pulse or other waveform component to be counteracted by a signal with identical morphology and opposing polarity; symmetric signals (such as those of FIGS. 6–11, 15–17, and 19–20) are not always necessary. It is also possible, when charge balancing is desired, to continuously or periodically calculate the accumulated charge in each direction and ensure that the running total is at or near zero over a relatively long term and preferably, that it does not exceed a safety threshold even for a short time.

To minimize the risks associated with waveforms that are either unbalanced or that have a direct current component, it is advantageous to use electrodes having enhanced surface areas. This can be achieved by using a high surface area material like platinum black or titanium nitride as part or all of the electrode. Some experimenters have used iridium oxide advantageously for brain stimulation, and it could also be used here. See Weiland and Anderson, "Chronic Neural Stimulation with Thin-Film, Iridium Oxide Electrodes," *IEEE Transactions on Biomedical Engineering*, 47: 911–918 (2000).

Determination of Threshold Values

The following inventive procedures may be used to verify the effectiveness of the implanted neurostimulator and to determine various stimulation parameters for responsive and non-responsive stimulation.

For instance, to verify pulse parameters for effective termination of epileptiform activity after the neurostimulator has been implanted, the following procedure may be used. An epileptiform-inducing stimulation is introduced into the brain under physician control using the implanted neurostimulator to initiate epileptiform activity. A responsive stimulation described by the stimulation signal parameters outlined above, e.g., selected electrode, pulse width, pulse morphology, pulse-to-pulse interval, pulse amplitude, number of pulses in a burst, or continuous waveform, etc., is applied to the brain. The stimulation signal parameters may be varied and reapplied until the epileptiform activity ceases.

The steps of initiating epileptiform activity using the implanted neurostimulator, varying stimulation parameters, checking for stimulation effectiveness, and incrementing stimulation parameters may be repeated until a satisfactory cessation of the epileptiform activity is achieved.

Similarly, the efficacy or threshold values associated with operation of the nonresponsive mode may be determined. The efficacy of the non-responsive mode is determined by the physician providing increasingly more severe epileptiform-causing stimulation using the implanted neurostimulator until epileptiform activity (also known as "afterdischarges") begins. The more difficult it is to induce the epileptiform activity, the better the non-responsive mode is functioning. By increasing the length of the burst, and/or the amplitude of the pulses within a burst, it is possible for the physician to determine the ease or difficulty with which epileptiform activity may be induced. By comparing how resistant the brain is to the induction of epileptiform activity when the non-responsive stimulation is either activated or not, or with differing burst parameters for the non-responsive stimulation the physician can optimally set the parameters of the non-responsive stimulation.

It is also possible to actively monitor various electrophysiological parameters of the patient's brain to determine when to apply non-responsive or scheduled stimulation. Approaches to accomplish this are set forth in co-pending U.S. patent application Ser. No. 09/706,322 to Pless, entitled "PREDICTING SUSCEPTIBILITY TO NEUROLOGICAL DYSFUNCTION BASED ON MEASURED NEURAL ELECTROPHYSIOLOGY" and filed on Nov. 3, 2000, which is hereby incorporated by reference as though set forth in full herein. For example, if a patient's neural excitability or refractoriness is found to be unusually high, then one or more of the non-responsive stimulation waveforms described herein may be applied.

Implantable Neurostimulator

Figure 21:
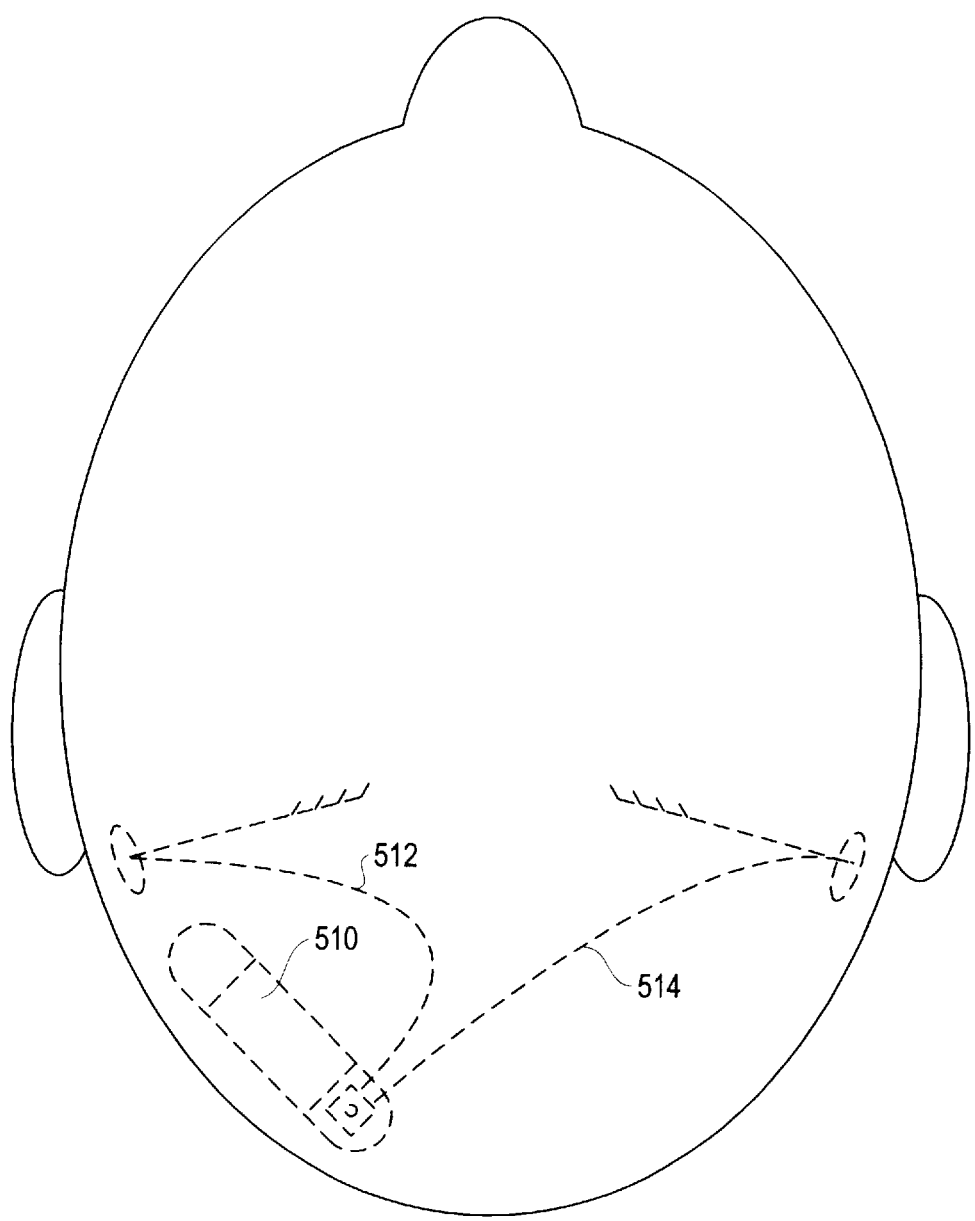
FIG. 21 is a simplified depiction of one embodiment of the inventive neurostimulator having multiple electrodes.

This inventive device includes a neurostimulator central unit and at least one electrode. The neurostimulator central unit includes the necessary circuitry, e.g., A/D converters, filters, central processing unit(s), digital processing circuits, blanking circuits, power supplies, batteries, signal generators, etc., and programming configured and adapted to perform the steps listed above. Specifically the neurostimulator central unit 510 desirably is as shown in FIG. 21 and is shaped in such a way that it conforms to the shape of the skull, although it need not be so. For details on advantageous configurations for the neurostimulator, see U.S. Pat. No. 6,016,449 to Fischell, et al., entitled "SYSTEM FOR TREATMENT OF NEUROLOGICAL DISORDERS" issued on Jan. 18, 2000, and Application Ser. No. 09/724,963 to Pless et al., entitled "FERRULE FOR CRANIAL IMPLANT" and filed on Nov. 28, 2000, both of which are hereby incorporated by reference as though set forth in full herein.

As will be described in further detail below, the neurostimulator central unit should at least contain a non-responsive electrical stimulation source, a responsive stimulation source, (where both sources may be the same circuit operated in two modes), and devices for detecting epileptiform activity and for initiating and for terminating the various non-responsive and responsive electrical stimulation. The neurostimulator assembly should also include at least a non-responsive neurostimulator lead 512 (which may also serve as a connection to a brain electrical activity sensor) and a responsive electrical neurostimulator lead 514, where both leads may in some circumstances be combined into the same lead unit. A detailed embodiment of this structure may be found in U.S. Pat. No. 6,016,449, referenced above. The various necessary connectors, leads, and supporting components are also included. The various sensor and neurostimulator functions may be incorporated into one or more electrodes as shown in FIG. 21, however. The various components perform the functions outlined above.

A highly desirable aspect of the inventive device is the use of multiple brain electrodes to provide therapy. The detecting electrodes are preferable in contact with the brain, but, as discussed above, may be scalp electrodes or within the brain tissue. Multiple therapy electrodes enhance the ability of electrical stimulation to desynchronize brain activity in terminating epileptiform activity. Although the same burst may be delivered from a multiplicity of electrodes in the vicinity of the epileptogenic focus, we prefer introducing bursts having different signal parameters, particularly pulse to pulse timing, to the brain from different electrodes to achieve a greater degree of spatial heterogeneity of neural activity and most effectively desynchronize brain activity.

We contemplate that this method of terminating epileptiform activity provides a substantial added benefit in that the lower current densities at the electrodes may be used to affect a larger amount of brain tissue than if a single electrode were used.

The application of multiple electrodes to different parts or regions of the brain also provides a way to treat epilepsy having more than one focus. Electrodes may be placed on or near the various epileptogenic foci. The inventive neurostimulator senses and stimulates independently from each electrode. Optional amplifier blanking and/or selective filtering eliminates cross talk, and logical flow in the device's software keeps the device from erroneously detecting its own output as epileptiform activity.

This inventive device may utilize independently actuatable, spatially separated electrodes so that those epilepsies having many epileptogenic foci or for which the focus is so diffuse the seizure arises from a large portion of the brain, may be treated. In such a case, it is desirable to place one electrode deep in the brain, preferably in the area of the hippocampus or thalamic structures. Additional electrodes may be placed on the surface of the cortex. When epileptiform activity is detected, the device stimulates from the hippocampal region to take advantage of the large number of neural pathways emanating from that area into the cortex. Electrodes on the cortex provide additional electrical access to the brain allowing electrical stimulation to terminate epileptiform activity having a greater spatial extent.

Figure 22:
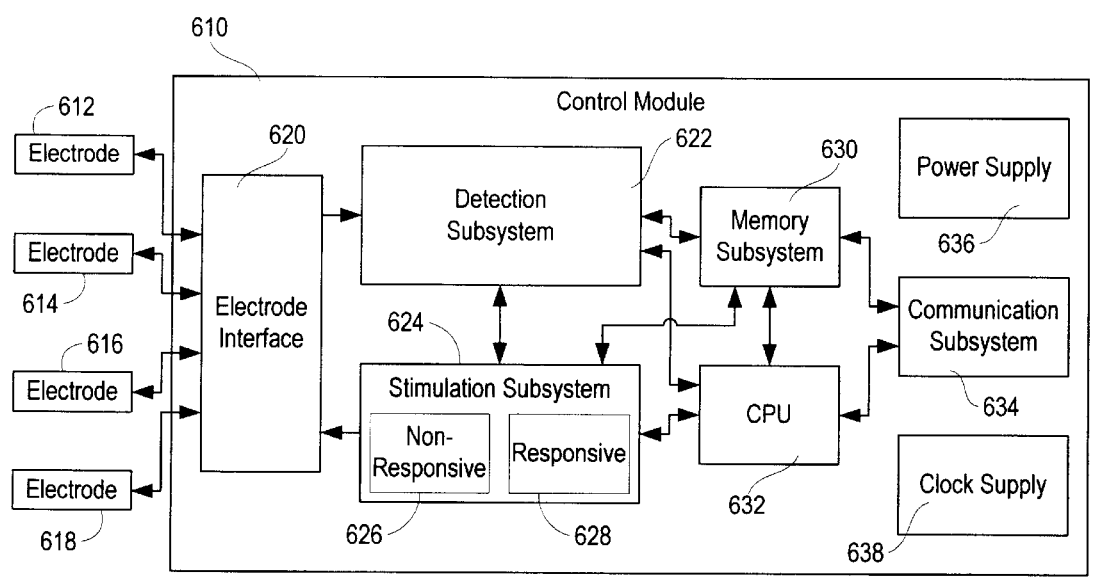
FIG. 22 is a block diagram of an exemplary neurostimulator according to the invention.

An overall block diagram of the neurostimulator device 510 used for measurement, detection, and treatment according to the invention is illustrated in FIG. 22. Inside a housing of the device 510 are several subsystems making up a control module 610. The control module 610 is capable of being coupled to a plurality of electrodes 612, 614, 616, and 618 (each of which may be connected to the control module 610 via a lead that is analogous or identical to the leads 512–514 of FIG. 21) for sensing and stimulation. As described above, in an embodiment of the invention, the electrodes 612–618 are fabricated with a high surface area treatment, coating, or material, such as platinum black, titanium nitride, or iridium oxide (among other possibilities), thereby facilitating the safe application of unbalanced signals or signals with small DC components.

Although four electrodes are shown in FIG. 22, it should be recognized that any number is possible, and in the embodiment described in detail below, eight electrodes plus the housing of the device 510 are used. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The electrodes 612–618 are connected to an electrode interface 620. Preferably, the electrode interface is capable of selecting each electrode as required for sensing and stimulation; accordingly the electrode interface is coupled to a detection subsystem 622 and a stimulation subsystem 624. The electrode interface also may provide any other features, capabilities, or aspects, including but not limited to amplification, isolation, and charge-balancing functions, that are required for a proper interface with neurological tissue and not provided by any other subsystem of the device 510.

The detection subsystem 622 includes an EEG analyzer function. The EEG analyzer function is adapted to receive EEG signals from the electrodes 612–618, through the electrode interface 620, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., incorporated by reference above; additional inventive methods are described in detail below. The detection subsystem may optionally also contain further sensing and detection capabilities, including but not limited to parameters derived from other physiological conditions (such as electrophysiological parameters, temperature, blood pressure, etc.).

The stimulation subsystem 624 is capable of applying electrical stimulation to neurological tissue through the electrodes 612–618. This can be accomplished in any of a number of different manners. For example, as described above, it is advantageous in some circumstances to provide stimulation in the form of a substantially continuous stream of pulses or waveform, or on a scheduled basis. This functionality is provided by a non-responsive portion 626 of the stimulation subsystem 624. Preferably, therapeutic stimulation is also provided by a responsive portion 628 of the stimulation subsystem 624 in response to abnormal events detected by the EEG analyzer function of the detection subsystem 622. As illustrated in FIG. 6, the stimulation subsystem 624 and the EEG analyzer function of the detection subsystem 622 are in communication; this facilitates the ability of stimulation subsystem 624 to provide responsive stimulation as well as an ability of the detection subsystem 622 to blank the amplifiers (or otherwise filter or process sensed signals) while stimulation is being performed to minimize stimulation artifacts. It is contemplated that the parameters of the stimulation signal (e.g., frequency, duration, waveform) provided by the stimulation subsystem 624 would be specified by other subsystems in the control module 610, as will be described in further detail below.

Also in the control module 610 is a memory subsystem 630 and a central processing unit (CPU) 632, which can take the form of a microcontroller. The memory subsystem is coupled to the detection subsystem 622 (e.g., for receiving and storing data representative of sensed EEG signals and evoked responses), the stimulation subsystem 624 (e.g., for providing stimulation waveforms and parameters to the stimulation subsystem), and the CPU 632, which can control the operation of the memory subsystem 630. In addition to the memory subsystem 630, the CPU 632 is also connected to the detection subsystem 622 and the stimulation subsystem 624 for direct control of those subsystems.

Also provided in the control module 610, and coupled to the memory subsystem 630 and the CPU 632, is a communication subsystem 634. The communication subsystem 634 enables communication between the device 510 (FIG. 21) and the outside world, particularly any external programmer used with the device. The disclosed embodiment of the communication subsystem 634 includes a telemetry coil (which may be situated outside of the housing of the device 510) enabling transmission and reception of signals, to or from an external apparatus, via inductive coupling. Alternative embodiments of the communication subsystem 634 could use an antenna for an RF link or an audio transducer for an audio link.

Rounding out the subsystems in the control module 610 are a power supply 636 and a clock supply 638. The power supply 636 supplies the voltages and currents necessary for each of the other subsystems. The clock supply 638 supplies substantially all of the other subsystems with any clock and timing signals necessary for their operation.

It should be observed that while the memory subsystem 630 is illustrated in FIG. 6 as a separate functional subsystem, the other subsystems may also require various amounts of memory to perform the functions described above and others. Furthermore, while the control module 610 is preferably a single physical unit contained within a single physical enclosure, namely the housing, it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 632 and the other functional subsystems may also vary—the functional distinctions illustrated in FIG. 6 may not reflect the integration of functions in a real-world system or method according to the invention.

Although preferred embodiments of the invention have been described herein, it will be recognized that a variety of changes and modifications can be made without departing from the spirit of the invention as found in the appended claims.

What is claimed is:

1. A method for treating a disorder in a brain of a patient, the method comprising the steps of:
   providing a non-responsive stimulation signal to the brain;
   detecting a neurological event; and
   providing a responsive stimulation signal in response to the neurological event;
   wherein the non-responsive stimulation signal is a non-pulsatile waveform.

2. The method for treating a disorder of claim 1, wherein the non-pulsatile waveform is substantially continuous.

3. The method for treating a disorder of claim 1, wherein the non-pulsatile waveform is a substantially sinusoidal waveform.

4. The method for treating a disorder of claim 1, wherein the non-pulsatile waveform is a quasi-sinusoidal waveform.

5. The method for treating a disorder of claim 1, wherein the non-pulsatile waveform is a substantially triangular waveform.

6. The method for treating a disorder of claim 1, wherein the non-pulsatile waveform is a substantially trapezoidal waveform.

7. The method for treating a disorder of claim 1, wherein the non-pulsatile waveform has a direct current component.

8. The method for treating a disorder of claim 7, wherein the non-pulsatile waveform is applied to at least one electrode having an enhanced surface area.

9. The method for treating a disorder of claim 1, wherein the non-pulsatile waveform is produced as a stepwise approximation of a desired waveform morphology.

10. The method for treating a disorder of claim 9, wherein the stepwise approximation is filtered.

11. The method for treating a disorder of claim 1, wherein the non-pulsatile waveform has a parameter.

12. The method for treating a disorder of claim 11, wherein the parameter is a frequency between approximately 0.5 Hz and approximately 15 Hz.

13. The method for treating a disorder of claim 11, wherein the parameter is a duration between approximately 0.05 minutes and approximately 60 minutes.

14. The method for treating a disorder of claim 11, wherein the parameter is variable.

15. The method for treating a disorder of claim 14, wherein the parameter is a frequency or an amplitude.

16. A method for treating a disorder in a brain of a patient, the method comprising the steps of:
   providing a non-responsive stimulation signal to the brain;
   detecting a neurological event; and
   providing a responsive stimulation signal in response to the neurological event;
   wherein the non-responsive stimulation signal is at least one substantially sinusoidal pulse.

17. A method for treating a disorder in a brain of a patient, the method comprising the steps of:
   providing a non-responsive stimulation signal to the brain;
   detecting a neurological event; and
   providing a responsive stimulation signal in response to the neurological event;
   wherein the non-responsive stimulation signal is at least one pulse having a waveform and an amplitude, and wherein the waveform has a derivative approaching zero as the amplitude approaches zero.

18. The method for treating a disorder of claim 17, wherein the waveform is substantially haversinusoidal.

19. A method for treating a disorder in a brain of a patient, the method comprising the steps of:
   providing a non-responsive stimulation signal to the brain;
   detecting a neurological event; and
   providing a responsive stimulation signal in response to the neurological event;
   wherein the non-responsive stimulation signal has a direct current component.

20. A method for treating a disorder in a brain of a patient, the method comprising the steps of:
   providing a non-responsive stimulation signal to the brain;
   receiving an input signal from the patient's brain while providing the non-responsive stimulation signal;
   filtering the input signal to remove an artifact of the non-responsive stimulation signal; and
   detecting a neurological event in the input signal.

21. The method for treating a disorder of claim 20, further comprising the step of providing a responsive stimulation signal in response to the neurological event.

22. The method for treating a disorder of claim 20, wherein the filtering step employs interference filtering.

23. The method for treating a disorder of claim 20, wherein the filtering step employs notch filtering.

24. An implantable neurostimulator for treating a disorder in a brain of a patient, comprising:
   a brain electrical activity sensor for sensing electrical activity in the brain;
   a brain electrical activity analyzer for detecting epileptiform activity in the electrical activity;
   a non-responsive electrical signal source adapted to deliver a non-responsive stimulation signal to a location in the patient's brain;
   a responsive electrical signal source adapted to deliver a responsive stimulation signal to a location in the patient's brain in response to the epileptiform activity;
   wherein the non-responsive stimulation signal is a substantially continuous non-pulsatile waveform, a waveform having at least one substantially sinusoidal pulse, a waveform having at least one pulse with a waveform and an amplitude and wherein the waveform has a derivative approaching zero as the amplitude approaches zero, or a waveform with a direct current component.

* * * * *